United States Patent [19]

Neeser et al.

[11] Patent Number: 5,198,352
[45] Date of Patent: Mar. 30, 1993

[54] PREPARATION OF ANTIBACTERIAL COMPOSITIONS FROM GLYCOPEPTIDES

[75] Inventors: Jean-Richard Neeser, Lausanne; Pierre Würsch, La Tour-de-Peilz, both of Switzerland

[73] Assignee: Nestec S.A., Vevey, Switzerland

[21] Appl. No.: 951,933

[22] Filed: Sep. 25, 1992

Related U.S. Application Data

[60] Continuation of Ser. No. 516,441, Apr. 30, 1990, abandoned, which is a division of Ser. No. 785,914, Oct. 9, 1985, Pat. No. 4,939,123.

[30] Foreign Application Priority Data

Oct. 26, 1984 [CH] Switzerland ............ 5136/84

[51] Int. Cl.$^5$ ............................. C12P 19/04
[52] U.S. Cl. ................... 435/101; 435/68.1; 435/85; 435/99; 435/219; 435/267; 530/370; 530/395; 530/402; 536/124; 536/128; 536/53
[58] Field of Search ............ 435/101, 68.1, 85, 99, 435/219, 267; 530/370, 395, 402; 536/22, 55.2, 124, 188

[56] References Cited

FOREIGN PATENT DOCUMENTS 89940 9/1983 European Pat. Off. .............. 514/58

OTHER PUBLICATIONS

Yamaucki et al., Agr. Biol. Chem., vol. 39(4), 1975, pp. 873–878.
Tai et al., J. Biol. Chem., vol. 250(21), 1975, pp. 8569–8575.
Shemer et al., Cereal Chem., vol. 55(3), 1978, pp. 383–391.
Tarentino et al., Methods in Enzymology (V. Gilsburg ed. Acad. Press-1978) pp. 574–580.
Nesser et al., Analytical Biochem., vol. 142, 1984, pp. 58–67.
Pusztai et al., Biochem. Biophysica Acta, vol. 207, 1970, pp. 413–431.
Pierce-Cretel, FEMS Micro. Letters vol. 20, 1983, pp. 237–242.
Katagirl et al., Carbohydrate Res., vol. 128, 1983, pp. 283–292.

*Primary Examiner*—Ronald W. Griffin
*Assistant Examiner*—Pamela S. Webber
*Attorney, Agent, or Firm*—Vogt & O'Donnell

[57] ABSTRACT

Antibacterially active compositions are prepared from a proteolytic enzymatic digestate of glycopeptides obtained from a protein isolate enriched with soya glycoprotein 7S or with bean glycoprotein II. The glycopeptide digestate is treated with endo-$\beta$-N-acetylglucosaminidase H to obtain oligosaccharide compositions which then also may be treated with exo-$\alpha$-mannosidase to obtain further oligosaccharide compositions.

6 Claims, No Drawings

PREPARATION OF ANTIBACTERIAL COMPOSITIONS FROM GLYCOPEPTIDES

CROSS REFERENCE TO RELATED APPLICATIONS

This application is a continuation application of application Ser. No. 07/516,441, filed Apr. 30, 1990, now abandoned, which, in turn, is a divisional application of application Ser. No. 06/785,914, filed Oct. 9, 1985, now U.S. Pat. No. 4,939,123.

BACKGROUND OF THE INVENTION

This invention relates to an antibacterial composition for pathogenic bacteria provided with type I fimbriae, containing glycopeptides and/or oligosaccharides as active constituents, and to a process for preparing these active constituents.

There is little doubt that the majority of natural infections begin by the adherence of the pathogenic agent to the epithelial cells of the mucous membranes which enables the pathogenic agent to be implanted in and to colonize the animal tissue. In the process of infection by bacteria provided with protein structures known as "type I fimbriae", the adherence of these bacteria to the animal cells being termed "sensitive to mannose", these structures recognize specific receptors which are complex glucidic groups, probably oligomannoside chains forming part of the glycoconjugates in the surface of the cellular membranes.

It has recently been shown (see N. Firon et al., Carbohydr. Res. 120 (1983) pp. 235-249) that the phenomenon of adherence of bacteria provided with type I fimbriae to the epithelial cells and their ability to cause the hemagglutination of erythrocytes in guinea pigs may be inhibited in the presence of certain oligosaccharides resembling the specific structure of the membranal receptors, the bacteria thus being lured into preferentially fixing the oligosaccharides in question. These oligosaccharides are either obtained by synthesis or are isolated from the urine of patients having enzymatic deficiencies.

In the same vein, published European Patent Application No. 89940, for example, relates to a composition containing the structure Gal$\alpha$1→3Gal which is chemically obtained and which is capable of inhibiting "in vitro" the adherence of Escherichia coli K88+ to the intestinal cells of young pigs.

SUMMARY OF THE INVENTION

The object of the present invention is to provide a composition containing as active constituents glycopeptides and/or oligosaccharides of vegetable or animal origin obtained enzymatically and being capable of replacing the normal receptor recognized by the type I fimbriae and thus of inhibiting or reversing the adherence of the pathogenic bacteria provided with these fimbriae to the animal cells.

The composition according to the invention is characterized in that it contains as active constituent a glycopeptide and/or an oligosaccharide corresponding to the following formula:

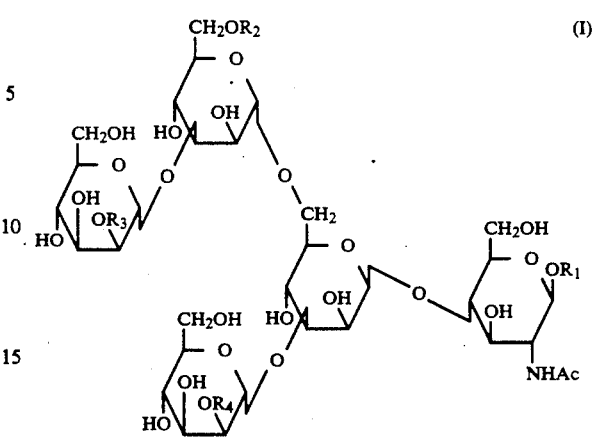

in which $R_1$ is a hydrogen atom, a residue 4GlcNAc$\beta$1→ASN or a residue

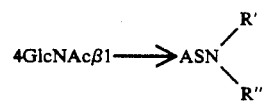

where R' and R" are the same or different and represent amino acid residues or polypeptide chains; $R_2$, $R_3$ and $R_4$ are the same or different and represent hydrogen atoms, mannose residues or oligomannoside chains.

Examples of pathogenic bacteria provided with type I fimbriae are pathogenic strains of Escherichia coli, Klebsiella pneumoniae, Salmonella typhimurium, Shigella flexneri, etc.

In formula (I) above, 4GlcNAc$\beta$1→ASN represents a 2-desoxy glucose ring which is attached to the terminal glucosamine in the 4 position, carries an acetylamino group in the 2 position and is attached in the 1 position with the $\beta$ configuration to the asparagine which may be substituted by amino acids or polypeptide chains.

The present invention also relates to a process for preparing the compounds of formula I, characterized in that a glycoprotein of vegetable origin is subjected to digestion with a proteolytic enzyme, in that the glycopeptides obtained are optionally converted into oligosaccharides by the action of an endo-$\beta$-N-acetylglucosaminidase H and in that the glycopeptides or the oligosaccharides obtained are then optionally subjected to controlled digestion with an exo-$\alpha$-mannosidase in order preferentially to cleave the $\alpha$1→2 bonds between two mannose residues.

Any vegetable flour known to contain reserve glycoproteins rich in oligomannosides may be used as starting material. It is of advantage to use defatted soya or bean flour.

DESCRIPTION OF PREFERRED EMBODIMENTS

A preferred group, particularly for its inhibiting effect on the adherence of pathogenic coliform enterobacteria, is represented by the glycopeptides of formula I above, in which $R_1$ is 4GlcNAc$\beta$1→ASN or

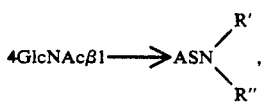

where R' and R" have the above meanings; $R_3$ and $R_4$ are hydrogen atoms and $R_2$ is a hydrogen atom or a mannose residue.

A preferred oligosaccharide, particularly for its inhibiting effect on pathogenic coliform enterobacteria, is the oligosaccharide of formula I in which $R_1$, $R_3$ and $R_4$ are hydrogen atoms and $R_2$ is a hydrogen atom or a mannose residue.

In the process of the present invention it is preferred to use an isolate enriched with soya glycoprotein 7S or bean glycoprotein II by extraction of the defatted flour at an alkaline pH (8-9), followed by selective precipitation of the glycoprotein at pH 4.5-5, for example using a method similar to that described in the literature (see M. Shemer, et al., Cereal Chem. 55 (1978), pp. 383-391 and A. Pusztai, et al., Biochem., Biophys. Acta 207 (1979), pp. 413-431).

To obtain glycopeptides, the fraction enriched with glycoprotein is then subjected to digestion with a proteolytic enzyme, for example using a method similar to that described in the literature (see F. Yamauchi, et al. Agr. Biol. Chem. 39 (1975), pp. 873-878).

The enzymatic digestion may be carried out with any active proteolytic enzyme at an acid, neutral or alkaline pH. The enzyme may be of fungal origin, microbial origin (for example, pronase, alkalase), vegetable origin (for example bromelin, ficin, papain) or animal origin (for example, trypsin, pepsin, pancreatin).

In a first embodiment of the process according to the invention intended for the preparation of oligosaccharides from glycopeptides, the above digestate is treated with an endo-β-N-acetylglucosaminidase H intended selectively to cleave the β1→4 bond between the two N-acetylglucosamine residues of formula I, thus converting $R_1$ into H.

In a preferred variant of this first embodiment of the process according to the invention, which is intended to shorten the oligomannoside chains of the above oligosaccharides to increase their activity, the oligosaccharides are subjected to a controlled treatment with an exo-α-mannosidase, an enzyme which preferentially cleaves the α1→2 bonds between two mannose residues, for example using a method similar to that described in the literature (see T. Tai, et al., J. Biol. Chem. 250 (1975), pp. 8569-8575).

In a second embodiment of the process according to the invention, which is preferred because it gives products showing greater activity than those obtained in the first embodiment, the oligomannoside chains are shortened by subjecting the above glycopeptides to a controlled treatment with an exo-α-mannosidase. Alternatively, the corresponding oligosaccharides may then be prepared by treating these glycopeptides with an endo H.

The compositions according to the invention may be used for the prophylaxis, treatment or diagnosis of infectious diseases caused by bacteria provided with type I fimbriae, more especially gastro-intestinal illnesses caused by coliform enterobacteria, such as *Escherichia coli* for example, and may be presented in a form adapted to the mode of administration and use.

For oral or enteral administration for example, the active constituent may be formulated as a syrup, pill, capsule, tablet, dragee, solution, suspension, emulsion or powder capable of reconstitution by the addition of an aqueous medium, for example, preferably in the form of a dietetic product, for example, a milk powder.

For parenteral administration, it may be formulated as a physically stabilized, sterile and apyrogenic solution or suspension.

For topical administration, for example for an ophthalmological application, it may be formulated as a solution, aerosol, ointment or unguent.

When the active constituent is intended for the diagnosis, identification or isolation of pathogenic bacteria, it will advantageously be coupled, preferably by covalent bonding, to a macromolecular support.

Finally, the compositions according to the invention may be used for disinfecting surfaces, for example in the form of solutions or emulsions for treating contact lenses.

In these compositions, the active constituent may represent from 0.1 to 90% by weight.

EXAMPLES

The invention is illustrated by the following Examples in which the parts and percentages are by weight, unless otherwise indicated.

In Examples 1 to 3 below, proof of the structure of the active constituents of formula I derives from the following characteristics:

a) Analysis of the glucidic composition of the starting glycoproteins reveals the presence of only two monosaccharide constituents, namely mannose and glucosamine. The oligosaccharides formed from these two constituents are attached to the polypeptide chain by the nitrogen of an asparagine (N-glycosidic bond), the "endo" part of these oligosaccharides thus corresponding to the following structure:

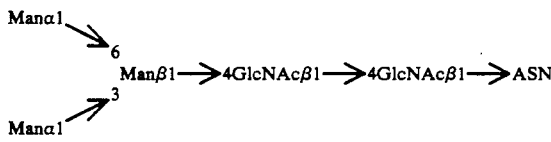

b) The fact that all the glycopeptide substrates are completely hydrolyzed by the endo-β-N-acetylglucosaminidase H (Endo H) proves that they all correspond to the minimum structure required for such an enzymatic digestion (see Tarentino, et al., Methods in Enzymology 50 (V. Ginsburg, ed.), Academic Press, New York (1978) pp. 574-580):

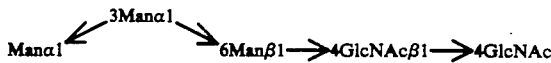

The superposition of the two above structures leads to the formulation of the proposed general structure.

EXAMPLE 1 a) Glycoprotein: A fraction enriched with glycoprotein 7S is prepared from defatted soya flour by extraction at pH 8.0 with a 0.5 mmolar solution of $Na_2SO_3$, precipitation at pH 5.7 to remove a first fraction (rich in 11S) and a second precipitation at pH 4.5, followed by two washings at the same pH which gives the fraction enriched with 7S.

b) Glycopeptides: The enzymatic digestion of the protein fraction is carried out from 30 g of protein in 2 liters of tris-HCl buffer solution (0.05 molar, pH 8.0) in the presence of toluene for 24 hours at 40° C. using 600 mg of PRONASE E (Merck AG) and then for 48 hours using another 300 mg of enzyme. The glycopeptides are isolated after filtration of this solution, passing the eluate over DOWEX 50W-X8 resin (H+ form), washing the resin with distilled water until the glucides have disappeared from the washing waters and neutralizing the combined fractions with an AMBERLITE IRA 400 resin ($CO^{--}_3$ form). The final solution is concentrated and freeze-dried and the product may finally be purified by fractionation in a column of SEPHADEX G-25. The overall yield of the process is 88% (based on the final quantity of mannose present in the glycopeptide mixture). Analysis of the glucidic composition of the mixture obtained as described above (by the method described in J. R. Neeser, et al., Anal. Biochem. (1984)) revealed the presence of an average of 7.6 units of mannose for two units of N-acetylglucosamine.

c) Oligosaccharides: The glycopeptides isolated as described above proved to be completely digestible with endo-$\beta$-N-acetylglucosaminidase H (ENDO H, Seikagaku Kogyo Co. Ltd.), this latter property forming the basis of the process used to obtain the corresponding oligosaccharides: a glycopeptide sample containing 7.5 mg of oligomannoside is dissolved in 10 ml of citrate-phosphate buffer solution (pH 6.0, 10 mmolar) and 100 milliunits of ENDO H (unit defined by the manufacturer) and 0.5 ml of toluene are added to the resulting solution. After incubation for 24 hours at 37° C., the enzyme is denatured by heating. The hydrolysate thus obtained may be used in this form (crude) for hemagglutination tests (see Example 4 below). The same hydrolysate may also be treated with an AMBERLITE MB 3 resin (H+ and OH− form) in order to isolate the oligosaccharides thus liberated: after addition, agitation and decantation of the resin, it is washed with distilled water until the glucides have disappeared from the washing waters and the combined fractions are concentrated. Analysis of the oligosaccharides thus purified revealed the presence of 7 to 8 mannose units for one N-acetylglucosamine unit for a product containing 85% of mannose, the overall yield of the enzymatic hydrolysis and isolation of the oligosaccharides being substantially quantitative. Analysis by high-performance thin-layer chromatography (HPTLC) of the crude product of the digestion with Endo H and of the mixture of the purified oligosaccharides gives similar results: the enzyme releases three different products corresponding to the structures GlcNAc-(Man)$_6$ (18%), GlcNAc-(Man)$_7$ (26%) and GlcNac-(Man)$_8$ (56%) (Man representing a mannose residue), these carbohydrates being completely released from the starting glycopeptides.

EXAMPLE 2 a) Glycoprotein: A fraction enriched with glycoprotein II is prepared from ground and defatted kidney bean—(*Phaseolus vulgaris*) flour by extraction at pH 9.0 and dialysis against acidified water at pH 5.0, resulting in precipitation of the glycoprotein fraction which is separated and redissolved at pH 8.0. The fraction rich in glycoprotein II is obtained after the combined supernatants have been centrifuged twice and freeze-dried.

b) Glycopeptides: The enzymatic digestion of the protein fraction is carried out in exactly the same way as from soya glycoprotein 7S (Example 1b above). Analysis of the glucidic composition of the mixture obtained (see J. R. Neeser, et al., Anal. Biochem. (1984)) revealed the presence of an average of 7.8 units of mannose for two units of N-acetylglucosamine.

c) Oligosaccharides: The glycopeptides isolated as described above proved to be completely digestible with Endo H. The enzymatic hydrolysis and isolation of the oligosaccharides are carried out in exactly the same way as from the soya glycopeptides (see Example 1c above). In this case, analysis by HPTLC revealed the liberation of 5 different products corresponding to the structures GlcNAc-(Man)$_5$ (5%), GlcNAc-(Man)$_6$ (10%), GlcNAc-(Man)$_7$ (26%), GlcNAc-(Man)$_8$ (15%) and GlcNAc-(Man)$_9$ (44%).

EXAMPLE 3

In order to produce glycopeptides and oligosaccharides of reduced structure from the products of Examples 1 and 2, use is made of the ability of $\alpha$-mannosidase (from *canavalia*, Canavalia, Sigma Chemical Company) to cleave the Man$\alpha$1→2 bonds preferentially to the Man$\alpha$1→3 Man bonds.

A sample of glycopeptides containing 350 mg of oligomannoside originating from soya glycoprotein 7S (Example 1b above) is dissolved in 75 ml of citrate buffer solution (0.01 molar, pH 4.5) and 190 units of $\alpha$-mannosidase (from *canavalia*, unit defined by the manufacturers) are added to the resulting solution. After incubation for 1 hour at 25° C., the mixture is scalded, cooled and filtered. The filtrate is then freeze-dried. The freeze-dried product may be used as such (crude) for hemagglutination tests (see Example 4 below). It may also be purified in a column of SEPHADEX G-25 in order effectively to separate the glycopeptide mixture and the mannose released by the enzyme.

Analysis of the glucidic composition of the product (see J. R. Neeser, et al., Anal. Bioch. (1984)) revealed the presence of 4.8 units of mannose for two of N-acetylglucosamine.

Analysis by HPTLC of the products obtained as described above, but from the corresponding oligosaccharides of vegetable origin (Examples 1c and 2c above), confirms that a compound corresponding to the formula GlcNAc-(Man)$_5$ is indeed the principal constituent of the mixtures obtained.

EXAMPLE 4

Inhibition of the Hemagglutination of Erythrocytes in Guinea Pigs by Adherent Strains of *E. coli* in the Presence of Glycopeptides and Oligosaccharides Two adherent strains of *E. coli* were used systematically in hemagglutination tests and hemagglutination inhibition tests, namely: a clinical isolate of *E. coli* 16375 (Univ.-Klinik für Kinderheilkunde, Innsbruck) and the strain *E. coli* 0119.K69,L74-30 (K69). These bacteria were washed with saline water (0.9% NaCl) and the suspensions were adjusted to a concentration of $10^9$ bacteria/ml (by optical density measurement).

The guinea pig erythrocytes were suspended in saline water in a concentration of 1%.

The hemagglutination and hemagglutination inhibition tests were carried out by mixing 25 $\mu$l (microliter) of the bacterial suspension, 50 $\mu$l of the erythrocyte suspension and 25 μl of a saline solution (respectively free from or containing an inhibitor, in which case several different concentrations were tested in series). The readings were made after standing for 2 hours at 4° C.

The results are shown in Table I below:

TABLE I

| | Inhibition of erythrocyte hemagglutination in guinea pigs | | | | |
|---|---|---|---|---|---|
| | Concentration[a] (ppm of oligomannoside) | | Concentration[b] (μ-molarity) | | |
| Inhibitor | E. coli 16375 | E. coli K 69 | E. coli 16375 | E. coli K 69 | Activity relative to α-MM |
| Methyl-α-D-mannoside (α-MM) | 125 | 60 | 650 | 325 | 1 |
| Glycopeptides Endo-H digestate (crude) purified oligosaccharides } from the glycoprotein 7S of soya seeds | 130/150 | 65/75 | 100 | 50 | 6.5 |
| Glycopeptides Endo-H digestate (crude) purified oligosaccharides } from the glycoprotein II of bean seeds | 125 | 60 | 90 | 45 | 7 |
| Mixture of the glycopeptides of ovalbumin[c] | 40/60 | 20/30 | 70 | 35 | 10 |
| GP IV | 95 | n.t. | 90 | n.t. | 7.5 |
| GP V | 10/15 | 5 | 12 | 6 | 60 |
| Oligosaccharides (from soya glycopr. 7S) digested (1h) with α-mannosidase | 10/25 | 10/15 | 18 | 12 | 30 |
| Oligosaccharides (from bean glycopr. II) digested (1h) with α-mannosidase | 10/25 | 10 | 18 | 12 | 30 |
| Manα1→3 Manβ1→4 GlcNAc (of synthetic origin)[d] | 7.5 | 5.5 | 20 | 15 | 25 |
| Glycopeptides (from soya glycopr. 7S) digested (1h) with α-mannosidase | 12/18 | 6/9 | 15 | 7.5 | 40 |
| Glycopeptides (from bean glycopr. II) digested (1h) with α-mannosidase | 12/18 | 6/9 | 15 | 7.5 | 40 |

Table I, legend:

a) Minimum inhibiting concentration in the final mixture resulting in complete inhibition of hemagglutination.

b) Calculated expression of the concentration of inhibitor from the formula (mean in the case of mixtures) derived from analysis of the glucidic composition of the product.

c) The products GP IV and V correspond to the carbohydrates attached to an asparagine obtained, separated and named in accordance with the literature (see T. Tai, et al., J. Biol. Chem. 250 (1975), pp. 8569–8575). The mixture of the glycopeptides from ovalbumin corresponds to that described (see T. Tai, et al., J. Biol. Chem. 250 (1975), pp. 8569–8575).

d) Synthetic product kindly offered by Prof. Dr. Hans Paulsen (Institut für Organische Chemie und Biochemie der Universität Hamburg).

n.t. means not tested.

Other experiences have shown that the vegetable glycopeptides have a comparable inhibiting effect on the hemagglutination of guinea pig erythrocytes caused by the enteropathogenic strains E. coli 086.K61,B74-10 and 0111.K58,B75-44.

EXAMPLE 5

Adherence and Adherence Inhibition of Enteropathoqenic E. coli 16375 to Human Buccal Cells Cells were collected by taking smears from the mouth of a member of the laboratory staff, washed 4 times with a phosphate-buffered physiological salt solution (NaCl 0.15 molar, phosphate 0.01 molar, (PBS)) and finally diluted to a concentration of $10^6$ cells/ml. The enteropathogenic bacteria E. coli of the clinical isolate 16375 were washed twice with PBS and diluted to a concentration of $2.10^9$ bacteria/ml.

The incubations were carried out by mixing 500 μl of the cell suspension, 250 μl of the bacterial suspension and 250 μl of PBS (for measuring adherence) or an inhibitor (a series of different concentrations being tested for measuring inhibition). Mixing was carried out by slow rotation for 30 minutes at ambient temperature. Four washings with PBS (5 ml) then preceded the collection of smears and the Gram stainings. The number of adhering bacteria per cell was counted under an optical microscope, 50 cells per test being analyzed. The results are shown in Table II below:

TABLE II

| Inhibitor | Concentration (ppm equivalent mannoside) | % adherence inhibition |
|---|---|---|
| Methyl-α-D-mannoside: | 100 | 70 |
| | 50 | 45 |
| | 10 | 35 |
| Glycopeptides from soya glycoprotein 7S (Example 1b) | 100 | 65 |
| | 50 | 30 |
| | 10 | 25 |
| Glycopeptides from soya glycoprotein 7S digested (1h) with α-mannosidase (Example 3) | 100 | 90 |
| | 25 | 77 |
| | 5 | 21 |

EXAMPLE 6

Fixing of Glycopeptides to a Solid Support

The glycopeptides produced by the digestions with pronase (Examples 1b and 2b) may be fixed to Sepharose gel by the following method: 2 g of SEPHAROSE 6MB activated with CNBr (Pharmacia Fine Chemicals) were washed with a solution of HCl (1 mmolar, 400 ml) and filtered. At the same time, 63 mg (dry weight, containing 25 mg of oligomannoside) of glycopeptides from the bean glycoprotein II (Example 2b) were dissolved in a buffer solution of $NaHCO_3$ (0.1 molar, pH 8.3) containing NaCl (0.5 molar). Mixing of the glycopeptide solution and the suspended gel was carried out by slow rotation for 2 hours at ambient temperature. Successive washings with $NaHCO_3$/NaCl buffer, with an ethanolamine solution (2 hours at ambient temperature), with more $NaHCO_3$/NaCl buffer, with an acetate buffer solution (0.1 molar, pH 4.0) containing NaCl (0.5 molar) and finally with more $NaHCO_3$/NaCl buffer lead to the gel coupled to the glycopeptides. The yield of the reaction was a fixing of 48% (based on the dosage of mannose).

EXAMPLE 7

Diagnosis Test for Identifying Bacteria having Specific Acceptors for the Structures of the Active Constituents a) Bacteria are mixed with guinea pig erythrocytes for a hemagglutination test in accordance with Example 4. At the same time, a similar mixture is prepared with the addition of a solution of one of the biologically active products (in a sufficient concentration to cause complete inhibition in accordance with Table I). A reading confirming the hemagglutination of erythrocytes by the bacterial suspension and its inhibition by addition of one of the active constituents will provide the proof that the bacteria have specific acceptors for the structure of that constituent.

b) Alternatively, a mixture of a bacterial suspension and Sepharose gel coupled to the glycopeptides (Example 6) may be prepared on a microscope slide. After incubation for 15 minutes, analysis under an optical microscope shows that, if the bacteria have the specific acceptors, they cover the gel particles whereas, in the opposite case, the same particles do not fix any bacteria.

EXAMPLE 8

Isolation of Bacteria having Specific Acceptors for the Structures of the Active Constituents The Sepharose gel coupled with the glycopeptides obtained in accordance with Example 6 is introduced into a column. A mixture of bacteria is passed through that column, the bacteria having specific acceptors for the glycopeptides coupled with the gel being retained whilst the other bacteria are directly eluted. After rinsing, a buffer containing one of the active constituents is used for eluting the bacteria having specific acceptors in pure form.

We claim:

1. A process for preparing compounds having antibacterial activity comprising treating a protein isolate with a proteolytic enzyme to obtain a digestate, wherein the protein isolate is selected from the group consisting of protein isolates of defatted soya flour enriched with glycoprotein 7S and defatted kidney bean flour enriched with bean glycoprotein II, isolating glycopeptides from the digestate, treating the isolated glycopeptides with endo-$\beta$-N-acetylglucosaminidase H to form a hydrolysate and then isolating oligosaccharides from the hydrolysate.

2. A process according to claim 1 further comprising treating the isolated oligosaccharides with exo-$\alpha$-mannosidase to cleave $\alpha 1 \rightarrow 2$ bonds.

3. A process according to claim 1 wherein the proteolytic enzyme is PRONASE E.

4. A process according to claim 2 wherein the proteolytic enzyme is PRONASE E and the exo-$\alpha$-mannosidase is obtained from Canavalia.

5. A process for preparing compounds having antibacterial activity comprising treating a protein isolate with a proteolytic enzyme to obtain a digestate, wherein the protein isolate is selected from the group consisting of protein isolates of defatted soya flour enriched with glycoprotein 7S and defatted kidney beam flour enriched with glycoprotein II, isolating glycopeptides from the digestate and treating the isolated glycopeptides with exo-$\alpha$-mannosidase to cleave $\alpha 1 \rightarrow 2$ bonds.

6. A process according to claim 5 wherein the proteolytic enzyme is PRONASE E AND the exo-$\alpha$-mannosidase is obtained from Canavalia.

* * * * *

UNITED STATES PATENT AND TRADEMARK OFFICE
CERTIFICATE OF CORRECTION

PATENT NO. : 5,198,352

DATED : March 30, 1993

INVENTOR(S) : Jean-Richard NEESER, et al.

It is certified that error appears in the above-identified patent and that said Letters Patent is hereby corrected as shown below:

Column 7, line 56, "Enteropathoqenic" should be --Enteropathogenic--.

Column 10, line 28 (line 6 of claim 5), "beam" should be --bean--.

Signed and Sealed this

Seventh Day of December, 1993

*Attest:*

BRUCE LEHMAN

*Attesting Officer*  *Commissioner of Patents and Trademarks*